United States Patent [19]

Bambury et al.

[11] Patent Number: 5,357,013
[45] Date of Patent: * Oct. 18, 1994

[54] HYDROPHILIC OXYGEN PERMEABLE POLYMERS

[75] Inventors: Ronald E. Bambury, Fairport, N.Y.; Dong J. Choo, Seoul, Rep. of Korea

[73] Assignee: Bausch & Lomb Incorporated, Rochester, N.Y.

[*] Notice: The portion of the term of this patent subsequent to Mar. 20, 2007 has been disclaimed.

[21] Appl. No.: 947,080

[22] Filed: Sep. 17, 1992

Related U.S. Application Data

[60] Continuation of Ser. No. 479,316, Feb. 13, 1990, abandoned, which is a division of Ser. No. 153,901, Feb. 9, 1988, Pat. No. 4,910,277.

[51] Int. Cl.$^5$ .................. C08F 226/06; C08F 224/00; C08F 230/08
[52] U.S. Cl. ...................................... 526/260; 526/279
[58] Field of Search .............................. 526/260, 279

[56] References Cited

U.S. PATENT DOCUMENTS

| | | | |
|---|---|---|---|
| 2,793,223 | 5/1957 | Merker | 260/448.2 |
| 3,004,950 | 10/1961 | Tousignant | 260/46.5 |
| 3,511,894 | 5/1970 | Markert | 260/875 |
| 3,948,866 | 4/1976 | Pennewiss et al. | 525/56 |
| 4,153,641 | 5/1979 | Delchert | 260/827 |
| 4,414,375 | 11/1983 | Neefe | 526/260 |
| 4,451,619 | 5/1984 | Heilmann et al. | 525/379 |
| 4,576,973 | 3/1986 | Keil | 521/149 |
| 4,774,309 | 9/1988 | Green | 526/260 |
| 4,810,764 | 3/1989 | Friends et al. | 526/260 |
| 4,871,824 | 10/1989 | Heilmann et al. | 526/260 |
| 4,910,277 | 3/1990 | Bambury et al. | 526/260 |

Primary Examiner—Joseph L. Schofer
Assistant Examiner—Wu C. Cheng
Attorney, Agent, or Firm—Craig E. Larson

[57] ABSTRACT

Polymeric materials comprising novel wetting agents such as 2-isopropenyl-4,4-dimethyl-2-oxazolin-5-one, 2-vinyl-4,4-dimethyl-2-oxazolin-5-one, and the like.

3 Claims, No Drawings

HYDROPHILIC OXYGEN PERMEABLE POLYMERS

This is a continuation of copending application Ser. No. 07/479,316 filed on Feb. 13, 1990, now abandoned, which is a divisional of copending application Ser. No. 153,901 filed on Feb. 9, 1988 now U.S. Pat. No. 4,910,277.

FIELD OF INVENTION

This invention relates to polymeric materials useful in biomedical devices, especially contact lenses, which are the product of reaching mixture comprising oxazolones.

BACKGROUND

A number of types of polymeric materials are known to be useful in contact lens manufacture. In general contact lens materials can be thought to fall into one of the following classifications: soft hydrophilic, soft, non-hydrophilic, and a more recent development, hard gas permeable. Gas permeable materials typically comprise polymeric materials formed by copolymerizing polyorganosiloxane monomers with various other monomers. These polymeric materials possess high oxygen permeabilities which make them particularly attractive as contact lens materials. In general, they are not as hydrophilic as the soft hydrophilic materials, and thus they are not as easily "wetted". These soft, non-hydrogels are illustrated by the following patents:

U.S. Pat. No. 4,153,641 discloses acrylate functional endcapped polyorganosiloxanes which can be polymerized to form high oxygen permeable polymeric networks, or which can be copolymerized with other monomers to form high oxygen permeable copolymers. Specific comonomers disclosed include low esters of acrylic acid, a methacrylic acid, styryls and N-vinyl pyrrolidinone.

U.S. Pat. No. 4,208,506 discloses soft contact lenses made from polymers and copolymers comprising polyparaffinsiloxane polymers and copolymers formed by polymerizing a polyparaffinsiloxane monomer alpha, omega terminally bonded through divalent hydrocarbon groups to polymerized, free radical polymerizably activated, unsaturated groups forming a polymer in a crosslinked network. Additionally, specific comonomers are disclosed which include lower esters of acrylic and methacrylic acid, styryls and N-vinyl pyrrolidinone which may be copolymerized with the above-described polyparaffinsiloxane monomer to form a copolymer.

U.S. Pat. No. 4,303,772 discloses polysiloxanyl alkyl esters of acrylic and methacrylic acids and its copolymerization with alkyl esters of acrylic, methacrylic acids and/or itaconate esters to produce highly permeable contact lens material. The copolymer preferably includes a crosslinking agent and hydrophilic monomer. Contact lenses manufactured from the material are easily machined and polished into hard or semi-hard contact lenses having excellent dimensional stability.

U.S. Pat. No. 4,330,383 discloses improved contact lens materials are obtained from copolymers containing a siloxanyl alkyl ester vinyl monomer by exposing the materials to high energy radiation thereby reducing the amount of unreacted monomer and residual contaminants.

U.S. Pat. No. 4,327,203 discloses articles for biomedical applications made from a polymer formed by polymerizing (a) one or more polysiloxane monomers alpha, omega terminally bonded through divalent hydrocarbon groups to an activated, unsaturated group with (b) a cycloalkyl modulus modifier, e.g. tertiary butylcyclohexyl methacrylate, menthyl acrylate or methylisopentyl cyclooctyl acrylate, and (c) a tear film stabilizer. The products are useful as hard contact lenses. U.S. Pat. No. 4,341,889 discloses the modulus modifier above can be tertiary butyl styrene. U.S. Pat. No. 4,355,147 discloses the modulus modifier above can be a polycyclic acrylate or methacrylate such as isobornyl methacrylate, adamantyl acrylate or isopinocamphyl methacrylate.

U.S. Pat. No. 4,652,622 discloses polymeric materials comprised of monomeric polysiloxanes end capped with activated unsaturated groups, a modulus modifier and small amounts of an internal wetting agent such as N-alkenoyltrialkylsilyl aminate.

DETAILED DESCRIPTION OF THE INVENTION

The invention relates to polymeric materials which are particularly useful in contact lenses formed by polymerizing a mixture comprising:

a compound represented by the general formula

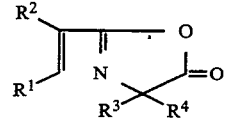

where $R^1$ and $R^2$ independently denote a hydrogen atom or a lower alkyl radical with one to six carbon atoms, and $R^3$ and $R^4$ independently denote alkyl radicals with one to six carbon atoms or a cycloalkyl radical with 5 or 6 carbon atoms.

Specific examples of these compounds include 2-isopropenyl-4,4-dimethyl-2-oxazolin-5-one (IPDMO), 2-vinyl-4,4-dimethyl-2-oxazolin-5-one (VDMO), spiro-4'-(2'isopropenyl-2'-oxazolin-5-one) cyclohexane (IPCO), cyclohexane-spiro-4'-(2'Vinyl-2'oxazol-5'-one) (VCO), and 2-(-1-propenyl)-4,4-dimethyl-oxazol-5-one (PDMO).

These compounds have two important features which make them particularly preferred comonomers with acrylate or methacrylate functional polysiloxane monomers: (1) They are relatively nonpolar and are thus highly compatible with polysiloxane monomers thus forming optically clear monomer mixtures and polymers, and (2) They are converted to highly polar amino acids upon mild hydrolysis. Thus they can be copolymerized into a hydrophobic polymeric matrix and then hydrolyzed to render the matrix substantially hydrophilic.

These compounds are prepared by the general reaction sequence:

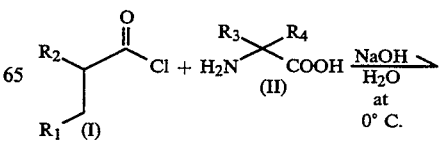

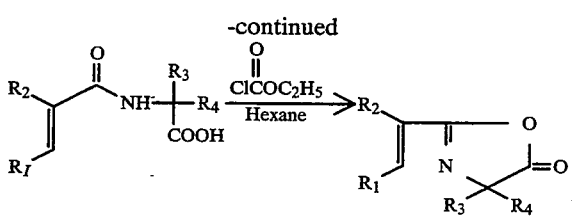

The first step being a Shotten-Bauman acylation of an amino acid. The polymerizable functionality is introduced by using either acryloyl or methacryloyl chloride. The second step involves a ring closure with a chloroformate to yield the desired oxazalone. The product is isolated and purified by the usual procedures of organic chemistry.

The compounds can be copolymerized with hydrophobic polysiloxane monomers to form polymeric materials which have high oxygen permeabilities. These polymeric materials may then be hydrolyzed in order to convert the oxazolone components into amino acids. In general, the hydrolysis step will follow the general reaction of:

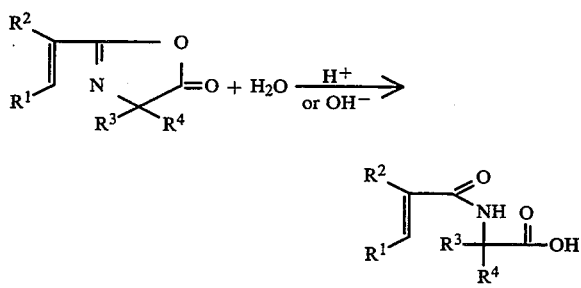

This reaction occurs mainly on the surface of the polymeric material and renders said surface hydrophilic. This hydrophilic surface is substantive due to the fact that the polymer network has been previously reacted with the carbon-carbon double bond between the $R^1$ and $R^2$ radicals (the schematic reaction above shows the double bond unreacted). Thus the above compounds can be referred to as wetting agents.

These wetting agents are far superior to state of the art internal wetting agents by virtue of their miscibility with polysiloxane monomers. Thus, they can be copolymerized in greater proportion than the state of the art wetting agents yielding materials which have hydrophilic surfaces.

Particularly useful hydrophobic monomers which can be copolymerized with the above wetting agents are acrylate or methacrylate functional endcapped polysiloxanes represented by the general formula:

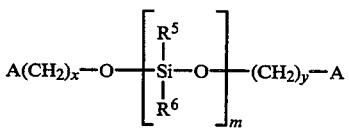

Where A denotes an acrylate or methacrylate radical, $R^5$ and $R^6$ independently denote alkyl radicals with one to six carbon atoms or phenyl radicals, x and y are on the average one to six, and m is at least one. In general the oxygen permeability of the copolymers will increase as the degree of polymerization of the polysiloxane monomer increases. However, as the degree of polymerization of the monomer increases, the copolymeric matrix will become more elastomeric. Toughening agents can be added to the prepolymerization mixture to add strength to the polymeric material.

Toughening agents are selected from the group comprising tertiary butyl styrene, cycloalkyl toughening agents, fluorinated methacrylate toughening agents, and polycyclic toughening agents.

The end-caps of the polymers used in the present invention besides being methacryl functional may also be end capped with any activated unsaturated group. The term "activated unsaturated group" refers to a group which has a substituent which functions through resonance to increase the free radical stability or activity of the double bond, thereby facilitating free radical polymerization of the monomer. These activated unsaturated groups become polymerized to form a polymer with a crosslinked three-dimensional network. Preferably the activating groups present are such that the monomers lend themselves to polymerization under mild conditions, such as ambient temperature. Preferred activating groups include: 2-cyanoacryloxy, acrylonitryl, acryloaminido, acryloxy, methacryloxy, styryl and N-vinyl-2-pyrrolidinone-x-yl where x may be 3, 4 or 5. The most preferred activating groups are methacryloxy and acryloxy.

The cycloalkyl toughening agents are described and defined in U.S. Pat. No. 4,327,203. These agents are a cycloalkyl acrylate or methacrylate of the formula

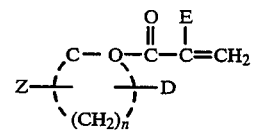

wherein
E is either hydrogen or methyl
D is branched or normal alkyl having 3 to 6 carbon atoms, preferably 3 to 4 carbon atoms
Z is either hydrogen or methyl and
n is an integer from 3 to 8 and preferably from 4 to 6.

Illustrative of the foregoing cycloalkyl toughening agents are the following: Menthyl methacrylate, menthyl acrylate, tertiarybutylcyclohexyl methacrylate, isopropylcyclopentyl acrylate, tertiarypentylcycloheptyl methacrylate, tertiarybutylcyclohexyl acrylate, isohexylcyclopentyl acrylate and methylisopentyl cyclooctyl acrylate.

The polycyclic toughening agents are described and defined in U.S. Pat. No. 4,355,147. These agents are a polycyclic acrylate or methacrylate selected from the group consisting of isobornyl acrylate, isobornyl methacrylate, dicyclopentadienyl acrylate, dicyclopentadienyl methacrylate, adamantyl acrylate, adamantyl methacrylate isopinocamphyl acrylate and isopinocamphyl methacrylate.

Illustrative of the fluorinated methacrylate toughening agents are: octafluoropentylmethacrylate, trifluoromethylmethacrylate, pentafluoroethyl methacrylate, and the like.

The toughening agent may be present in an amount from 90 to 10 parts by weight per 10 to 90 parts by weight of the above-described monomers. More preferably the modifier is present in the amount of 70 to 10 parts, more preferably yet the modifier is 45 to 15 parts.

The polymeric materials of the present invention are formed by: (1) mixing the monomers together; (2) adding a polymerization initiator; (3) subjecting the monomer/initiator mixture to a source of ultraviolet or actinic radiation and curing said mixture to a solid or elastomeric state.

Typical polymerization initiators include free radical generating polymerization initiators of the type illustrated by acetyl peroxide, lauroyl peroxide, decanoyl peroxide, coprylyl peroxide, benzoyl peroxide, tertiary butyl peroxypivalate, diisopropyl peroxycarbonate, tertiary butyl peroctoate, and $\alpha,\alpha$-azobis-isobutynnitrile. Ultraviolet free radical initiators illustrated by diethoxyacetophenone can also be used. The curing process will of course depend upon the initiator used and the physical characteristics of the comonomer mixture such as viscosity. In any event, the level of initiator employed will vary within the range of 0.01 to 2 weight percent of the mixture of monomers.

Typical formulations will comprise 1 to 98 weight percent polysiloxane monomer, 1 to 50 weight percent of the novel wetting agents, and 1 to 80 weight percent toughening agent. Preferably, the composition will comprise 60 to 95 weight percent polysiloxane monomer, 4 to 20 weight percent toughening agent and 1 to 20 weight percent of the novel wetting agent.

EXAMPLES

A. Synthesis of 2-isopropenyl-4,4-dimethyl-2-oxazolin-5-one (IPDMO)

1. Methacryloylation

In a 500 ml 3-neck round bottom flask equipped with a mechanical stirrer, thermometer and an addition funnel, 51.5 grams (0.5 mole) of $\alpha$-aminoisobutyric acid (Aldrich) and 40 grams (1 mole) of NaOH were dissolved in ~150 ml of $H_2O$. The reaction flask was cooled to 0° ~ −5° C. with MeOH-ice bath and 0.5 mole of methacryloyl chloride (distilled, Aldrich) was added dropwise while the temperature of the reaction mixture kept below 0° C. After stirring for an additional hour, the reaction mixture was acidified with concentrated HCl to a pH of about 3 to precipitate out the intermediate, which was then filtered, washed with cold $H_2O$ and air dried. Further drying was accomplished in vacuum oven at 80° C. overnight to obtain 44.9 grams (0.26 mole; 53%) n-methacryloyl-$\alpha$-aminoisobutyric acid (MAIBA), which was suitable for IPDMO synthesis. m.p. 157°–159° C.

2. Cyclization; Synthesis of IPDMO

In a 500 ml dry 3-neck round bottom flash, 0.26 mole of MAIBA was dispersed in 300 ml of dry hexane and allowed to react with 0.26 mole of alkylchloroformate with mechanical stirring by dropwise addition of triethylamine (0.52 mole) while the temperature of the reaction mixture was maintained at 45°~50° C. During the addition, the copious evolution of carbon dioxide and the formation of white precipitate of TEA-HCl were observed. The reaction mixture was stirred for an additional two hours. After cooling to room temperature, white precipitate was filtered off and hexane evaporated off yielding an oil. Pure IPDMO was obtained after two times of recrystallization in hexane at dry ice-acetone temperature. Yield was 29 grams (73%).

B. Synthesis of 2-vinyl-4,4-dimethyl-2-oxazolin-5-one (VDMO)

1. Acrylolation was achieved by adopting a procedure similar to step 1 of the synthesis of IPDMO except acryloyl chloride was used in place of methacryloyl chloride. The intermediate n-acryloyl-d-aminobutyric acid (AAIBA) was produced.

2. AAIBA was reacted with triethylamine and ethyl chloroformate in a fashion similar to step 2 of the synthesis of IPDMO to produce VDMO.

C. Synthesis of Spiro-4'-(2'-isopropenyl-2-oxazolin-5'-one) Cyclohexane (IPCO)

The synthetic method used to synthesize IPDMO was followed except 1-amino-1-cyclohexane carboxylic acid was used in place of $\alpha$-aminoisobutyric acid.

D. Synthesis of Spiro-4'-(2'-vinyl-2'-oxazolin-5'-one) Cyclohexane (VCO)

The synthetic method employed in the synthesis of VDMO was used except 1-amino-1-cyclohexane carboxylic acid was used in place of $\alpha$-aminoisobutyric acid.

E. Synthesis of 2-(1-propenyl)-4,4-dimethyl-oxazolin-5-one (PDMO)

The method employed in the synthesis of VDMO was employed except crotonyl chloride was used in place of methacryloyl chloride and $\alpha$-aminoisobutyric acid was used.

F. Synthesis and Characterization of Polymeric Materials

1. Polydimethylsiloxane Based Materials

Methacrylate end capped polydimethylsiloxane (PDMS) with an average degree of polymerization of about 180 was compounded with isobornylmethacrylate (IBOMA) and VDMO in the weight proportion of 85/5/5 (PDMS/IBOMA/VDMO). The mixture was stirred, a free radical initiator was added and polymerized by exposure to ultraviolet radiation. The resultant polymeric material was characterized for modulus, tensile strength, elongation, oleic acid uptake, and oxygen permeability ($D_K$). The material was purified by extraction with toluene and also the internal wetting agent (VDMO) was hydrolyzed in the polymeric material by boiling in buffered saline solution for 20 minutes. Both the toluene extracted sample and toluene extracted/hydrolyzed sample were characterized. The results of these tests are reported in Table 1.

TABLE 1

| | Polydimethylsiloxane Based Material | | | | |
|---|---|---|---|---|---|
| Material | Modulus (g/mm$^2$) | Tensile (g/mm$^2$) | Elongation % | Oleic % | $D_K$ |
| 95/5/5 (PDMS/IBOMA/VDMO) | 107 | 94 | 127 | 4.7 | 200 |
| toluene extracted | 521 | 142 | 35 | 4.4 | 200 |
| extracted/hydrolyzed | 908 | 199 | 37 | 6.0 | 200 |

Comparison with Prior Art Polymeric Materials

The polymeric material from Example F was immersed in a buffered solution for a period of time under controlled conditions. As a control polymeric material combining the wetting agents described by U.S. Pat. No. 4,652,622 was subjected to the same conditions and the wettability of each sample was monitored. The polymeric material of the present invention maintains its wettability to a greater degree than the state of the art wetting agent (the control).

What is claimed is:

1. A contact lens composition formed by polymerizing a mixture comprising a hydrophobic polysiloxane monomer and a wetting agent which is a compound represented by the general formula

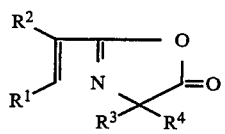

where $R^1$ and $R^2$ independently denote a hydrogen atom or a lower alkyl radical with one to six carbon atoms, and $R^3$ and $R^4$ independently denote alkyl radicals with one to six carbon atoms or a cycloalkyl radical with 5 or 6 carbon atoms; with the proviso that said hydrophobic monomer does not include a siloxane monomer represented by the formula

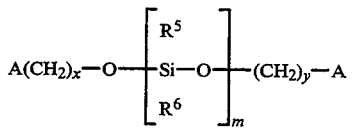

where A denotes an acrylate or methacrylate radical, $R^5$ and $R^6$ independently denote alkyl radicals with one to six carbon atoms or phenyl radicals, and x and y are on the average one to six.

2. The composition of claim 1 where the compound is 2-vinyl-4,4-dimethyl-2-oxazolin-5-one.

3. The composition of claim 1 where the compound is 2-isopropenyl-4,4-dimethyl-2-oxazolin-5-one.

* * * * *